United States Patent
Isaacs et al.

(10) Patent No.: US 8,518,110 B2
(45) Date of Patent: Aug. 27, 2013

(54) SYSTEM AND METHOD FOR STORING, SHIPPING AND INJECTING OCULAR DEVICES

(75) Inventors: Thomas L. Isaacs, Oldsmar, FL (US); Hayden Beatty, Dunedin, FL (US); William B. Wright, Anioch, TN (US); John Clough, St Pete Beach, FL (US)

(73) Assignee: Lenstec Barbados Inc.

( * ) Notice: Subject to any disclaimer, the term of this patent is extended or adjusted under 35 U.S.C. 154(b) by 693 days.

(21) Appl. No.: 12/554,345

(22) Filed: Sep. 4, 2009

(65) Prior Publication Data

US 2010/0036385 A1 Feb. 11, 2010

Related U.S. Application Data

(63) Continuation-in-part of application No. 11/525,360, filed on Sep. 22, 2006, now Pat. No. 8,435,288.

(51) Int. Cl.
*A61F 2/16* (2006.01)
*A61F 9/00* (2006.01)

(52) U.S. Cl.
USPC .......................................... 623/6.12; 606/107

(58) Field of Classification Search
USPC .................................. 606/107, 108; 623/6.12
See application file for complete search history.

(56) References Cited

U.S. PATENT DOCUMENTS

| | | | |
|---|---|---|---|
| 4,834,094 A | 5/1989 | Patton et al. | |
| 5,304,182 A | 4/1994 | Rheinish et al. | |
| 5,902,278 A | 5/1999 | Aguilar | |
| 6,174,315 B1 | 1/2001 | Chambers et al. | |
| 6,976,989 B1 | 12/2005 | Vincent | |
| 7,320,690 B2 | 1/2008 | Beavers et al. | |
| RE40,185 E | 3/2008 | Kikuchi et al. | |
| 2005/0125000 A1* | 6/2005 | Tourrette et al. | 606/107 |
| 2005/0149057 A1* | 7/2005 | Rathert | 606/107 |
| 2006/0235430 A1* | 10/2006 | Le et al. | 606/107 |
| 2008/0039862 A1* | 2/2008 | Tran | 606/107 |
| 2008/0077237 A1 | 3/2008 | Isaacs et al. | |

FOREIGN PATENT DOCUMENTS

| EP | 0711571 | 5/1996 |
|---|---|---|
| EP | 711571 A1 * | 5/1996 |
| WO | WO 2007098622 | 9/2007 |

OTHER PUBLICATIONS

IXEF polyarylamide; Solvay Advanced Polymers; Design and Molding Guide; Version 2.1; pp. 1 through 75.

* cited by examiner

*Primary Examiner* — Ryan Severson
*Assistant Examiner* — Ashley Fishback
(74) *Attorney, Agent, or Firm* — John J. Love; Claude Cooke, Jr.; Cooke Law Firm

(57) ABSTRACT

A shipping system for a medical device, such as implantable lens for an eye, is provided that may be reconfigured from a shipping mode into an injection mode without manually handling the contained lens or other device. Upon manufacture, a lens may be placed within the system assembly in the shipping configuration. While in the shipping configuration, the lens is kept in its desired shape and within a selected environment. Upon arrival at the destination, the user may attach fittings for injection of the device into a body. The process of changing from the shipping to the injection mode deforms the device into a shape suitable for injection. A new assembly for insertion of a medical device utilizing the shipping systems is also disclosed.

10 Claims, 14 Drawing Sheets

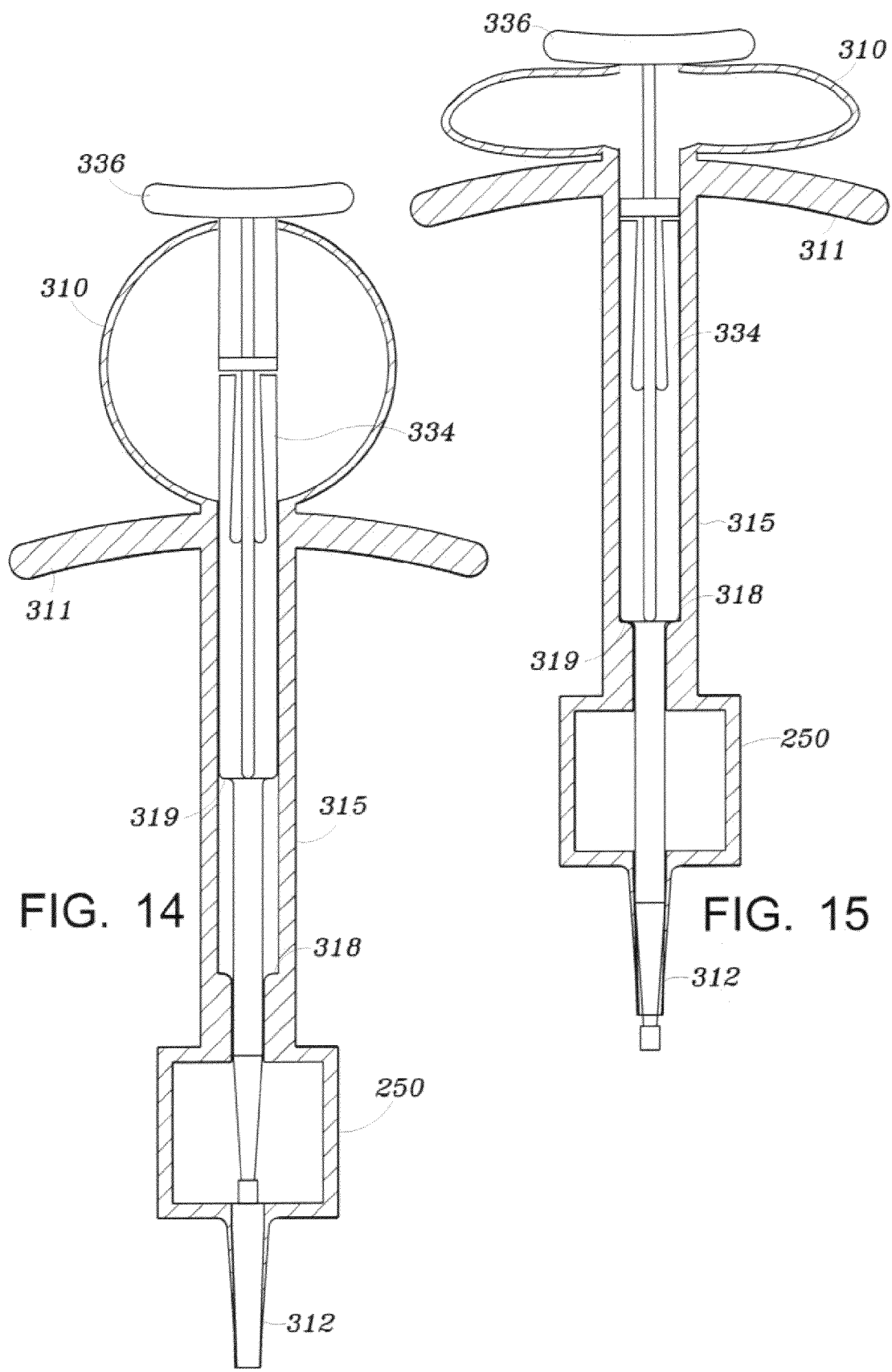

SYSTEM AND METHOD FOR STORING, SHIPPING AND INJECTING OCULAR DEVICES

This application is a continuation-in-part of application Ser. No. 11/525,360 filed on Sep. 22, 2006.

BACKGROUND OF THE INVENTION

1. Field of the Invention

This invention relates to medical apparatus. More specifically, this invention relates to a container for a foldable device, such as an intraocular lens, that enables a physician to inject the device directly into an eye without removing the device from the shipping container.

2. Description of Related Art

FIG. 1 shows the basic structure of an eye. Eye 20 has natural lens 10, which is partially exposed at pupil 12 underneath cornea 14. Around pupil 12 is iris 16. Lens 10 is attached to ciliary body 18 within sclera 22. Other tissue, such as choroid 24, retina 26 and fovea 28 are also present. Finally, optic nerve 30 carries optical signals from eye 20 to the brain.

For various reasons, such as cataract or injury, the natural lens of an eye may need replacement. Synthetic lenses for replacement are available from various manufacturers, who make the lens to the required optical characteristics. Intraocular lenses are made from three types of materials: silicone, hydrophobic (normally made of an acrylic) and hydrophilic. Silicone and acrylic lenses are shipped dry, whereas hydrophilic lenses are shipped in a wet condition. The index of refraction of the materials increases in the order: silicone, hydrophobic (acrylic) and hydrophilic. Hydrophilic lenses exhibit better biological compatibility and produce less inflammation after insertion into a patient's eye. While hydrophilic lenses are more beneficial, the cost and wet-storage requirements mean that, in many situations, lenses with a lower refractive index (but dry-shipped) are used instead of hydrophilic lenses. One of the advantages of dry-shipped lenses is that the lens can be shipped pre-loaded for injection.

Hydrophilic lenses are shipped in a sterile solution to preserve sterility and physical characteristics. Upon arrival at the medical facility, the lens is removed from its shipping container and placed in a device that is used to inject the lens into an eye. Unfortunately, the lens must be handled manually to transfer it from the shipping container to the injection device. The transfer from shipping container to the injection device introduces the potential for contamination of the lens. Moreover, the transfer procedure is often tedious and time-consuming. There is, therefore, a need in the art to eliminate problems associated with moving a lens from its shipping container to an injection device, thereby enabling greater use of hydrophilic intraocular lenses and other implantable devices.

SUMMARY OF INVENTION

The present invention is a shipping and storage container for a medical implant, such as a lens for an eye. The present invention is constructed and arranged so that it is quickly and efficiently reconfigured from a shipping mode into an injection device without manually handling the implant itself. Upon manufacture, the medical implant is placed within the present invention in its shipping configuration. While in the shipping configuration, the medical implant can be kept in its desired (undistorted) shape within a suitable fluid and protected by the body of the container. Upon arrival at the medical facility, a physician may attach one or more injection related fittings to the container (e.g., a syringe plunger and injection needle). The technician or physician may then operate the device to transition the container from the shipping configuration to the injection configuration. The injection configuration of the present invention forms the medical implant into a shape suitable for injection. The present invention thus obviates the need for a technician or physician to handle the medical implant directly before injection into the patient, thereby precluding a potential source of contamination and reducing the time necessary to perform the medical procedure. The present invention is generally applicable for medical devices that are folded before insertion into a patient.

The present invention may be susceptible to various modifications and alternative forms. Specific embodiments of the present invention are shown by way of example in the drawings and are described herein in detail. It should be understood, however, that the description set forth herein of specific embodiments is not intended to limit the present invention to the particular forms disclosed. Rather, all modifications, alternatives, and equivalents falling within the spirit and scope of the invention as defined by the appended claims are intended to be covered.

BRIEF DESCRIPTION OF DRAWINGS

Referring now to the drawings, the details of the preferred embodiments of the present invention are illustrated.

FIG. 14 is a cross sectional view of the housing with the plunger shown in a partially depressed position.

FIG. 15 is a cross sectional view of the housing of FIG. 10 with the plunger shown in a fully depressed position.

DETAILED DESCRIPTION

Figure 1:
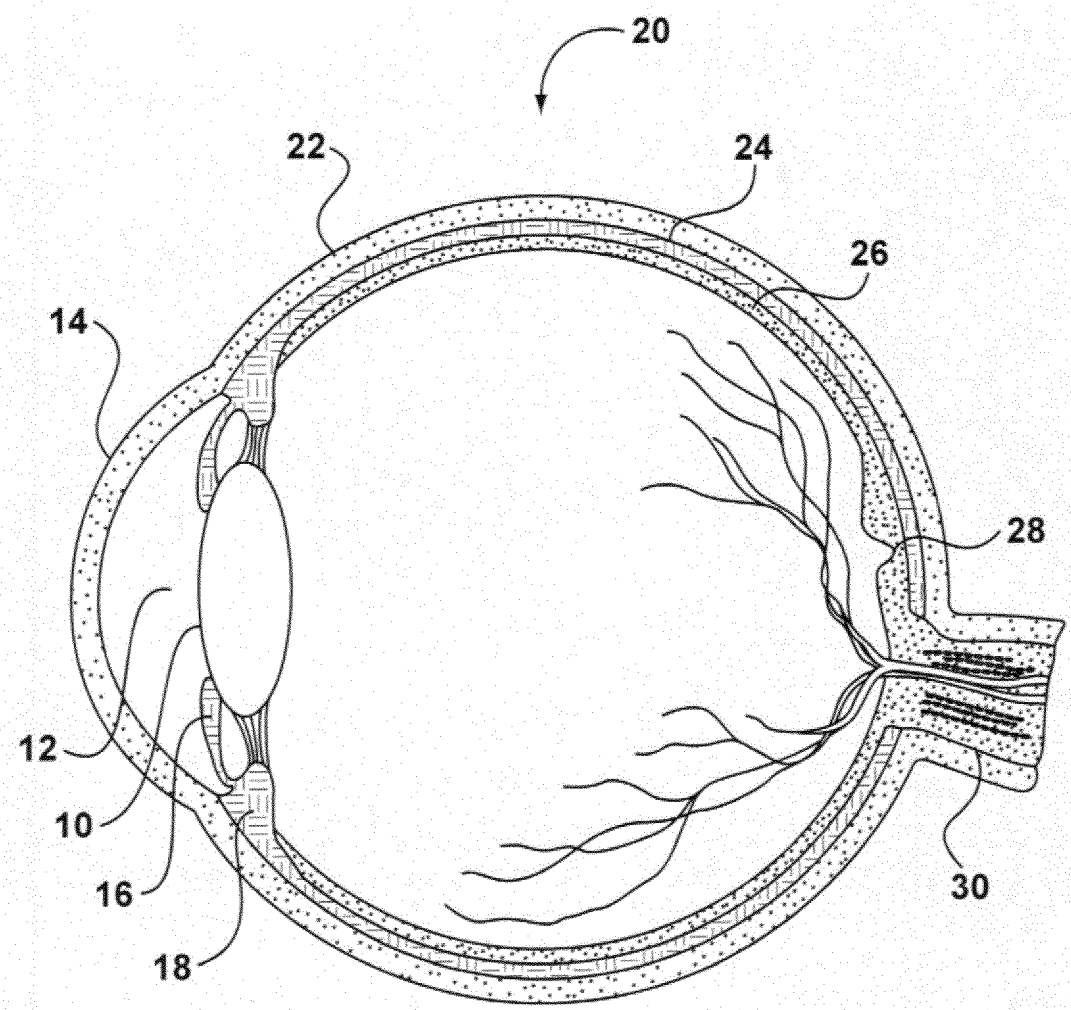
FIG. 1 is an illustration of an eye.

Referring now to the drawings, the details of exemplary embodiments of the present invention are schematically illustrated. Like elements in the drawings will be represented by like numbers.

Figure 2A:
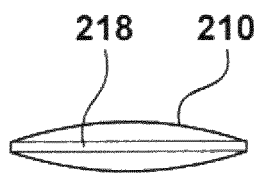
FIG. 2A is an end elevation view of one form of an intraocular lens.
Figure 2B:
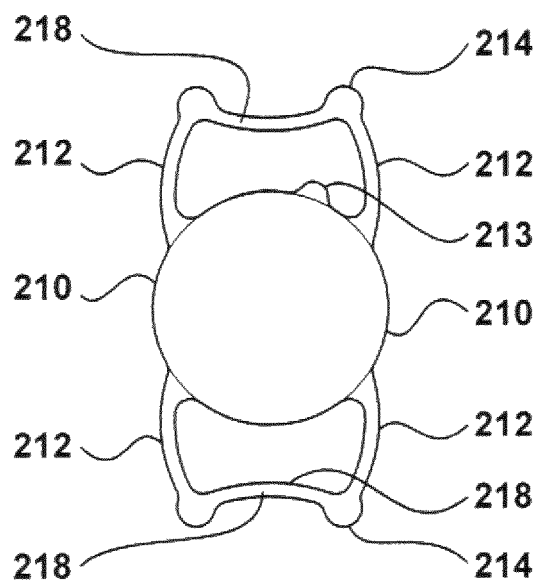
FIG. 2B is a plan view of the intraocular lens of FIG. 2A.

Referring to FIG. 2A, a front elevation view of an intraocular lens with optic 210 and haptic 218 is illustrated. A plan view of the lens and haptics is shown in FIG. 2B. The lens may have side plates 212, orientation tab 213 and foot plates 214.

Figure 3A:
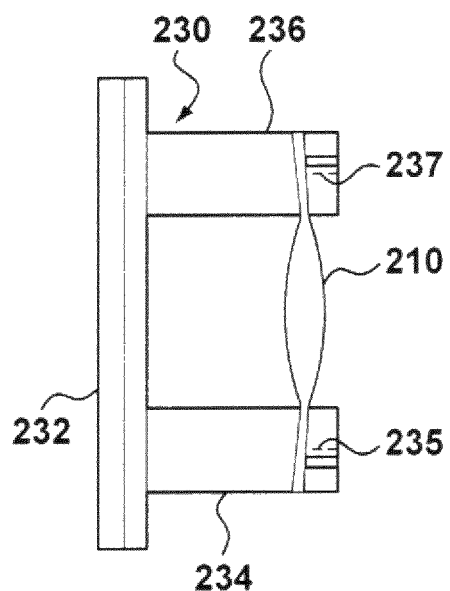
FIG. 3A is a side elevation view of an intraocular lens holder of one embodiment of the present invention.
Figure 3B:
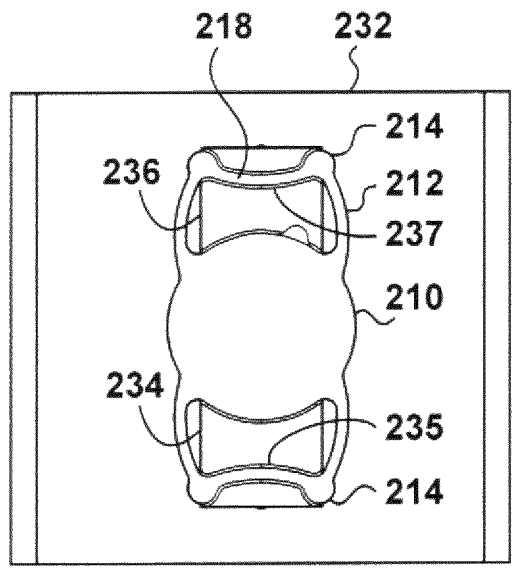
FIG. 3B is a plan view of the intraocular lens holder of FIG. 3A.
Figure 3C:
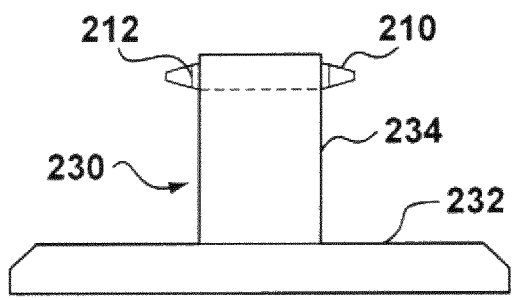
FIG. 3C is a front elevation view of the intraocular lens holder of FIG. 3A.

FIG. 3A shows optic 210 with its haptics fitted onto lens holder 230. Lens holder 230 has base 232 and legs 234 and 236. The legs have channels 235 and 237, respectively, within which lens haptics 218 are placed to secure the lens for shipping, as illustrated in FIG. 3B. FIG. 3C shows a front elevation view of optic 210 as it sits within the legs of lens holder 230. Lens holder 230 may be adapted for any lens or other device that is to be folded and inserted through an opening or incision into a patient.

Figure 4A:
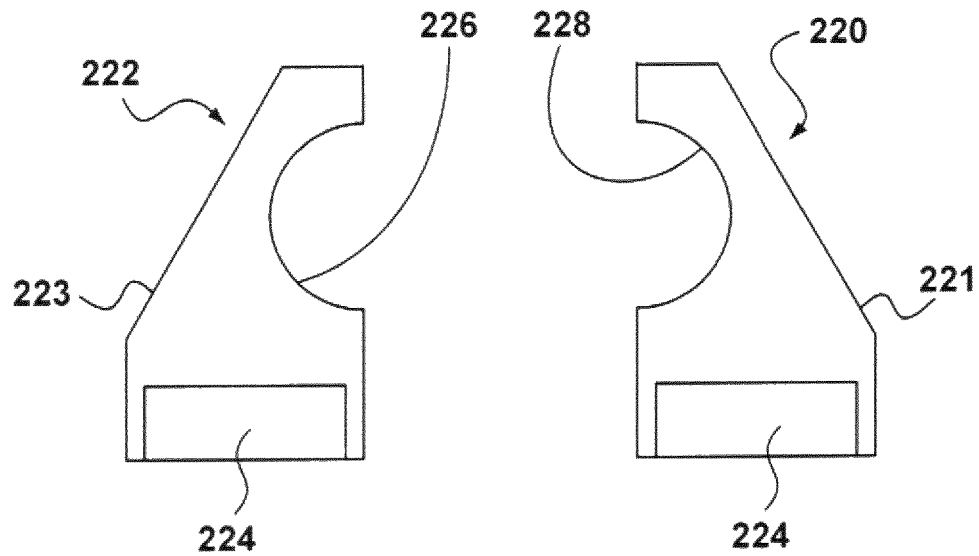
FIG. 4A is a front elevation view of one embodiment of folding guides in the transport configuration.
Figure 4B:
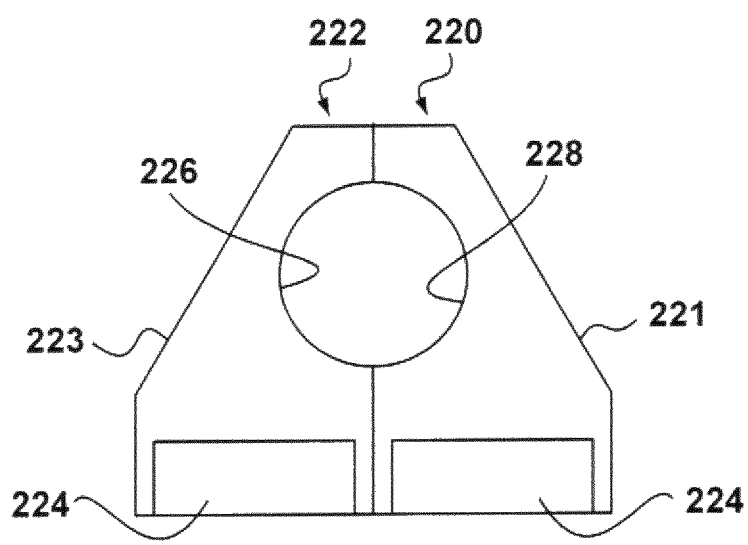
FIG. 4B is a front elevation view of one embodiment of folding guides in the injection configuration, after they have been moved to fold a device.

FIG. 4A illustrates lens folding guides 220 and 222. Right folding guide 220 has shoulder 221 and semi-cylindrical concave inner face 228. Left folding guide 222 may be a mirror image of right folding guide 220, with the former having shoulder 223 and semi-cylindrical concave face 226. Lens folding guides 220 and 222 may have keys 224, which are used to keep the folding guides oriented correctly during transition from the shipping mode to the injection mode, as described below. FIG. 4B shows the folding guides 220 and 220 in the injection mode, with the folding guides moved together. By forcing folding guides 220 and 222 together, respective concave faces 228 and 226 may force a lens to deform into a round cylinder, much like rolling one's tongue. In any case, a lens is deformed into a cylinder that is small enough to be inserted through an incision in an eye. If needed, friction-reducing additives may be used on surfaces to reduce friction as a lens or other device is deformed for insertion or is displaced from the folding guides.

Figure 5:
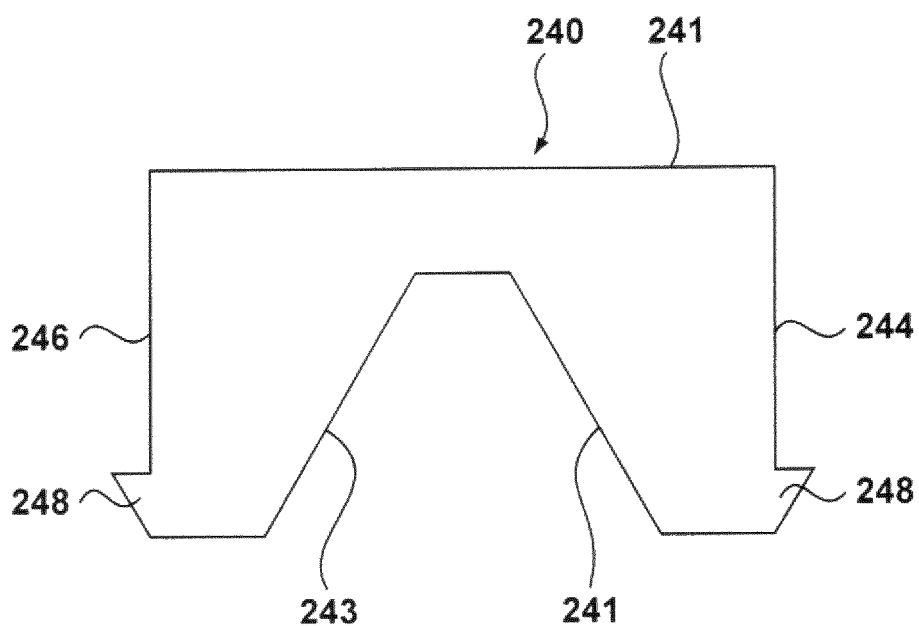
FIG. 5 is a front elevation view of the driving element of one embodiment of the invention.

FIG. 5 shows driving cam 240. Driving cam 240 has internal shoulders 241 and 243 that may be constructed and arranged to fit slideably against shoulders 221 and 223 of folding guides 220 and 222 (FIG. 4A). Driving cam 240 may have sides 244 and 246 that fit within a body, and two or more detent tabs 248.

Figure 6A:
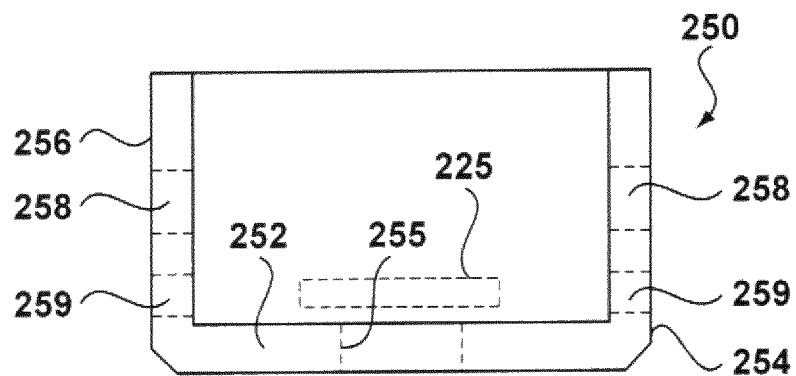
FIG. 6A is a front elevation view of the body of one embodiment of the invention.
Figure 6B:
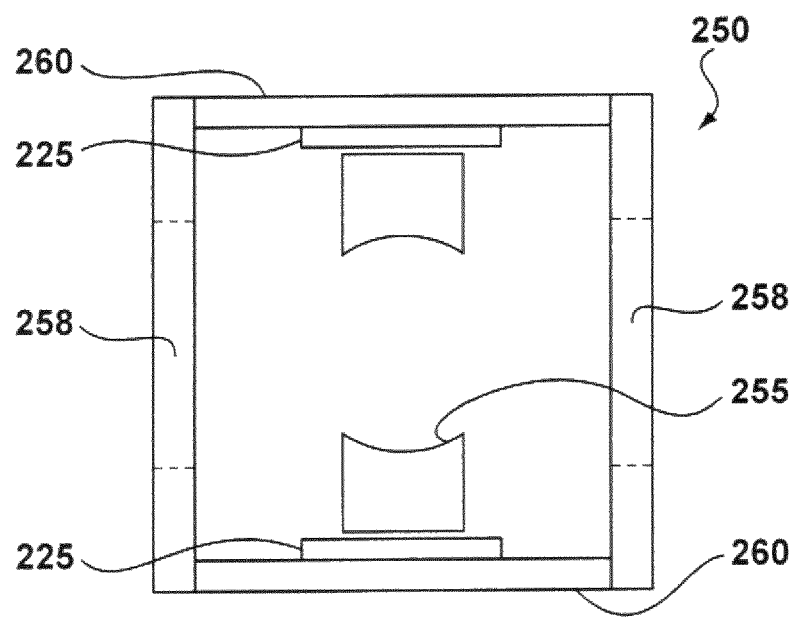
FIG. 6B is a plan view of the body of one embodiment of the invention with lens holder.

FIG. 6A is a front elevation view of "U" shaped body 250. Body 250 has a bottom 252 and sides 254 and 256 that mate with the sides 244 and 246, respectively, of driving cam 240 (FIG. 5). Each side 254 and 256 is fitted with a openings 258 and 259 into which the detents 248 of driving cam 240 fit. Body 250 has openings 255 within bottom 252 (FIG. 6B). Openings 255 are constructed and arranged to accommodate legs 234 and 236 of lens holder 230. Lens holder 230 may have any shape adapted to hold a foldable medical device. Front and back members 260 of body 250 may have attached thereto track guides 225, which may be disposed to allow key 224 (FIG. 4) to slide between track guide 225 and bottom 252 of body 250 as lens guides (FIG. 4) move to deform an implantable device before it is displaced from body 250. Although folding guides 220 and 222 are illustrated to form a cylindrical-shaped medical device after folding, it should be understood that other cross-sectional shapes may be formed, such as elliptical or rectangular.

Figure 7A:
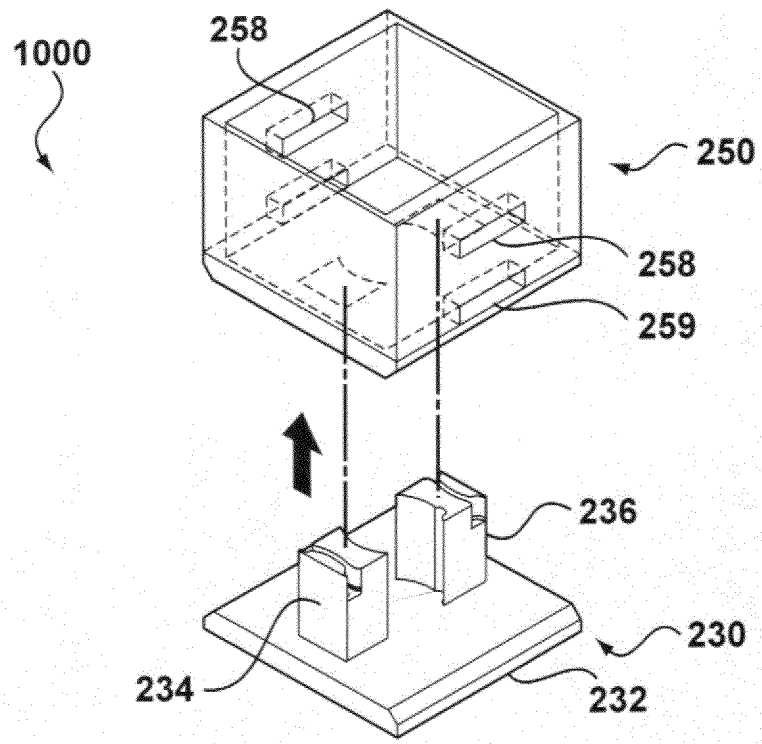
FIG. 7A is a perspective view showing placement of the lens holder in the bottom of the body to assemble the apparatus of the invention.

FIGS. 7A, 7B, 7C, 7D, 7E and 7F illustrate by isometric views the assembly and use of lens shipping, storage and injection system 1000. Referring to FIG. 7A, within injection system assembly 1000, body 250 is equipped with two rectangular upper shipping mode openings 258 and two rectangular lower injection mode openings 259. Each of openings 258 and 259 can be made of any convenient shape, but are intended to be constructed and arranged to accommodate tab 248 of driving cam 240 (FIG. 5), with one tab 248 within one hole 258 when assembly 1000 is in the shipping mode, and one tab 248 each within one hole 259 when assembly 1000 is in the injection mode. The shape of tab 248 is constructed and arranged to fit within either of the holes 258 and 259 so that the driving cam 240 can be moved from the shipping mode to the injection mode by deformation of either or both of driving cam 240 or sides 254 and 256 of body 250. While assembly 1000 may be disposable, alternate embodiments may be designed for reloading and reuse.

Figure 7B:
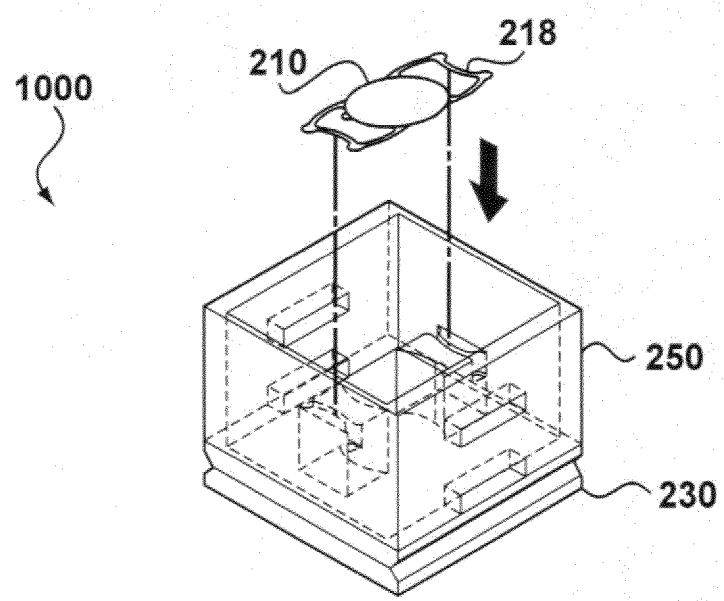
FIG. 7B is a perspective view showing placement of a lens in the lens holder.
Figure 7C:
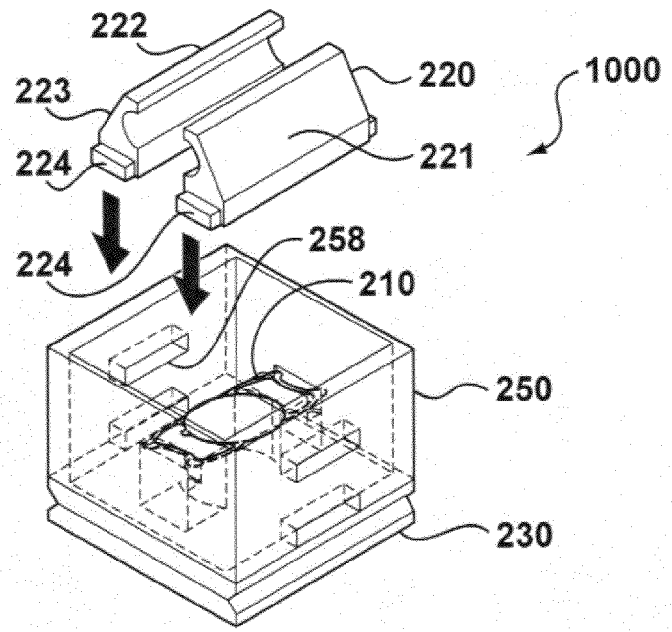
FIG. 7C is a perspective view showing placement of folding guides around the lens holder to assemble the apparatus of the invention.
Figure 7D:
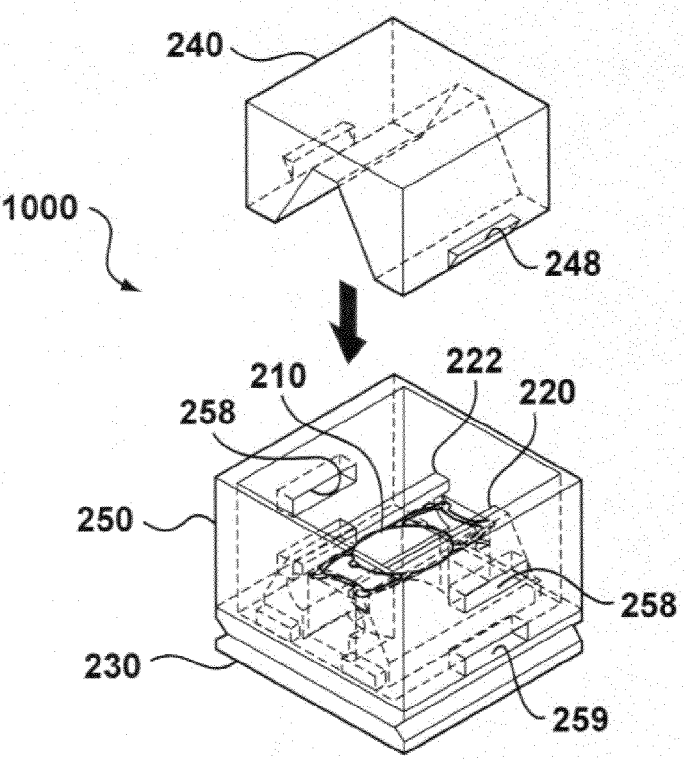
FIG. 7D is a perspective view showing placement of a driving element over the folding guides to assemble the apparatus of the invention.

Referring again to FIG. 7A, lens holder 230 may be inserted into body 250 through separate holes in bottom 230. Other shapes of lens holder 230 may be used. As illustrated in FIG. 7B, optic 210 and haptics 218 may then be placed on lens holder 230. Folding guides 220 and 222 may be placed within body 250, as illustrated in FIG. 7C. Then, driving cam 240 may be inserted into body 250, as illustrated in FIG. 7D until tabs 248 engage in the retaining slots 258, at which point system 1000 is in the shipping mode. The system may then be placed in a sealed container, which may contain a liquid suitable for storing and shipping the lens.

Figure 7E:
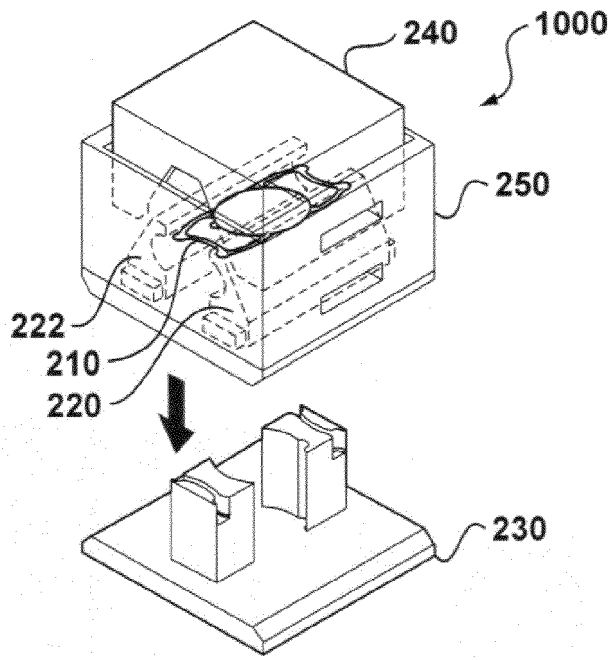
FIG. 7E is a perspective view of the apparatus showing removal of the lens holder.
Figure 7F:
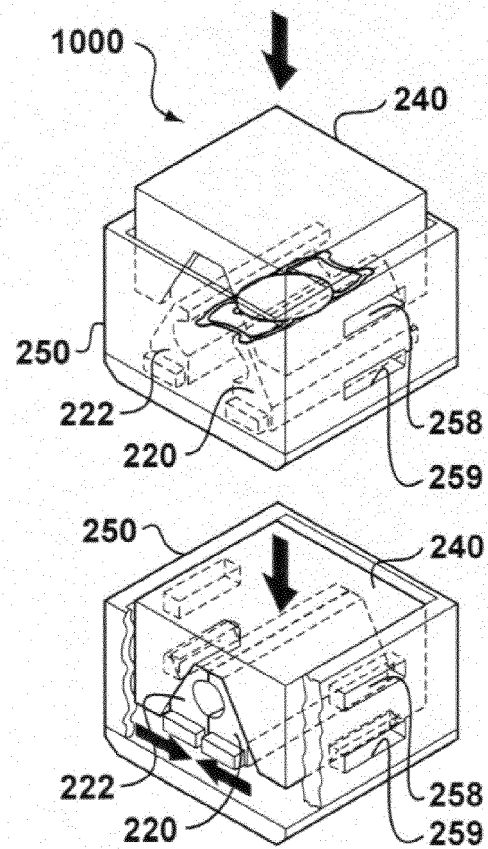
FIG. 7F is a perspective view of the apparatus showing closure of the folding guides.

Upon receipt of system 1000 by the user, the system 1000 must be transitioned from the shipping mode to the injection mode. To make the transition, the user simply removes lens holder 230 by detaching it from the bottom of the body 250, as illustrated in FIG. 7E. Once lens holder 230 is detached, the lens is suspended within body 250 between folding guides 220 and 222. The user then may depress driving cam 240 downward until tabs 248 are engaged with lower slots 259, as illustrated in FIG. 7F. In the process of depressing driving 240, folding guides 222 and 222 are pushed together as illustrated in the lower half of FIG. 7F. The inner concave shape of folding guides 220 and 222, within which sits optic 210, forces lens 210 to fold into a round shape that is suitable for injecting.

Figure 8A:
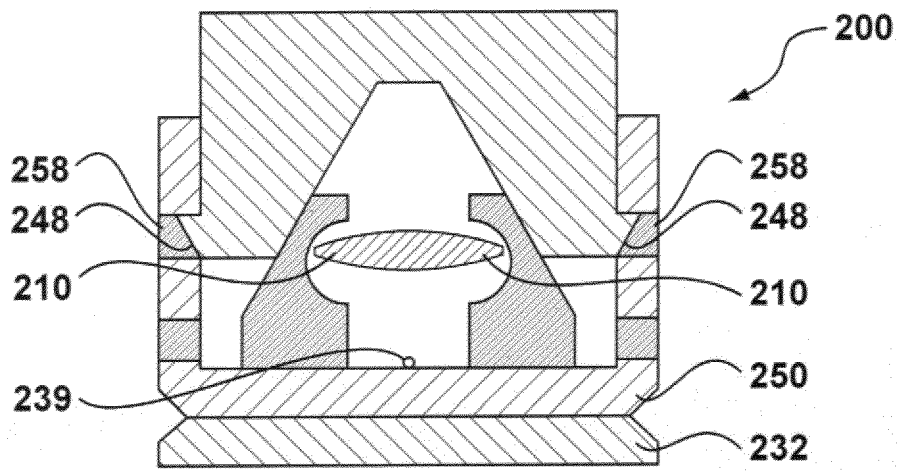
FIG. 8A is a center cross-section of the assembly of one embodiment of the invention in a shipping configuration.
Figure 8B:
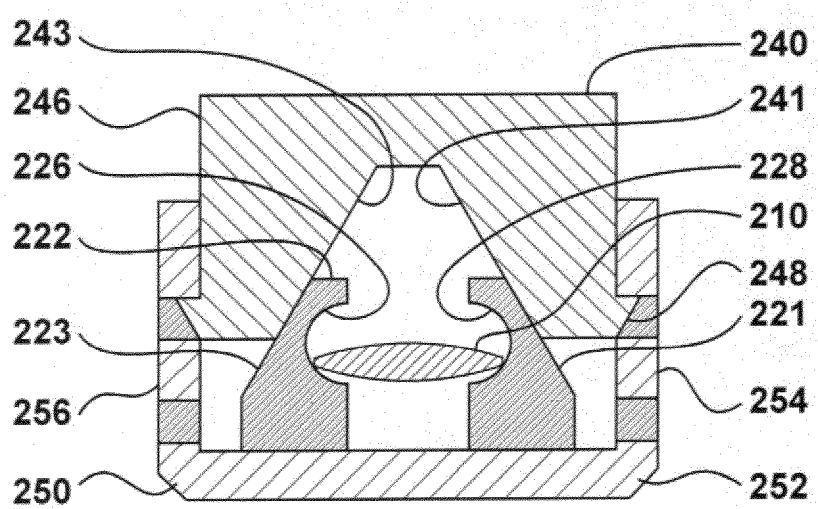
FIG. 8B is a center cross-section of the assembly of one embodiment of the invention after removal of the lens (or other device) holder.
Figure 8C:
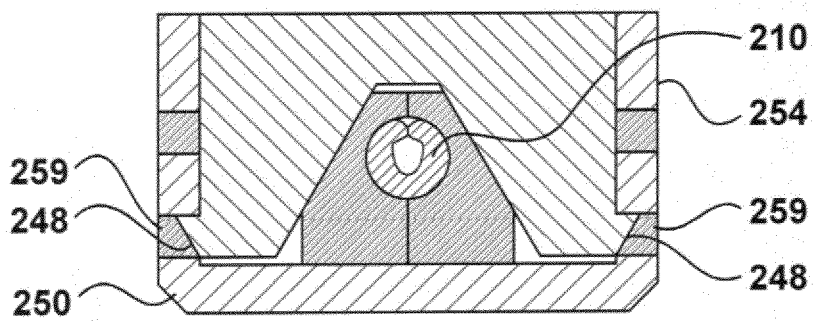
FIG. 8C is a center cross-section of the assembly of one embodiment of the invention after movement of the driving element to fold a lens.

FIGS. 8A, 8B and 8C show cross-sections halfway between front and back of the assembled device of system 1000. When assembly 1000 is received by the user, the first step in the preparation process is to remove lens holder 230 from body 250. To do so, the user grasps base 232 of lens holder 230 and pulls lens holder 230 away from the bottom of body 250 so that the legs 234 and 236 of the lens nest 230 are withdrawn through 250. During the removal step, lens 210, unable to slip out between the folding guides 220 and 222, is detached from lens holder 230 and comes to rest within the concave faces 226 and 228 of folding guides 222 and 220, respectively.

Referring to FIG. 8A, base 232 of lens holder 230 is shown at the bottom adjacent to the underside of the body 250. Locking nub 239 may be used to hold lens holder 230 in position within body 250. Detents 248 of driving cam 240 are locked within upper openings 258 of body 250 to secure driving cam 240 in the shipping mode. In FIG. 8B, lens holder 230 has been removed, as shown in FIG. 7E. Shoulder 223 of folding guide 222 is mated to the shoulder 243 of the driving cam 240.

Once lens holder 230 has been removed, the user may press down on the top of driving cam 240 until detents 248 move from upper holes 258 to lower holes 259. FIG. 8C shows the apparatus in the injection mode, after the user has moved the detents to the lower holes and the folding guides together. As lens 210 and haptics 212 are now contained within the concave faces 226 and 228, lens 210 and haptics 212 are rolled into the injection position as folding guides 220 and 222 are brought together. Once in the injection mode, an injection device, such as a syringe, can be attached to assembly 200 at one end, and an injection nozzle can be attached to the opposite end so that when the plunger of the syringe is operated, the lens is forced into the nozzle and then into a patient's eye, as shown in FIG. 9.

Figure 9:
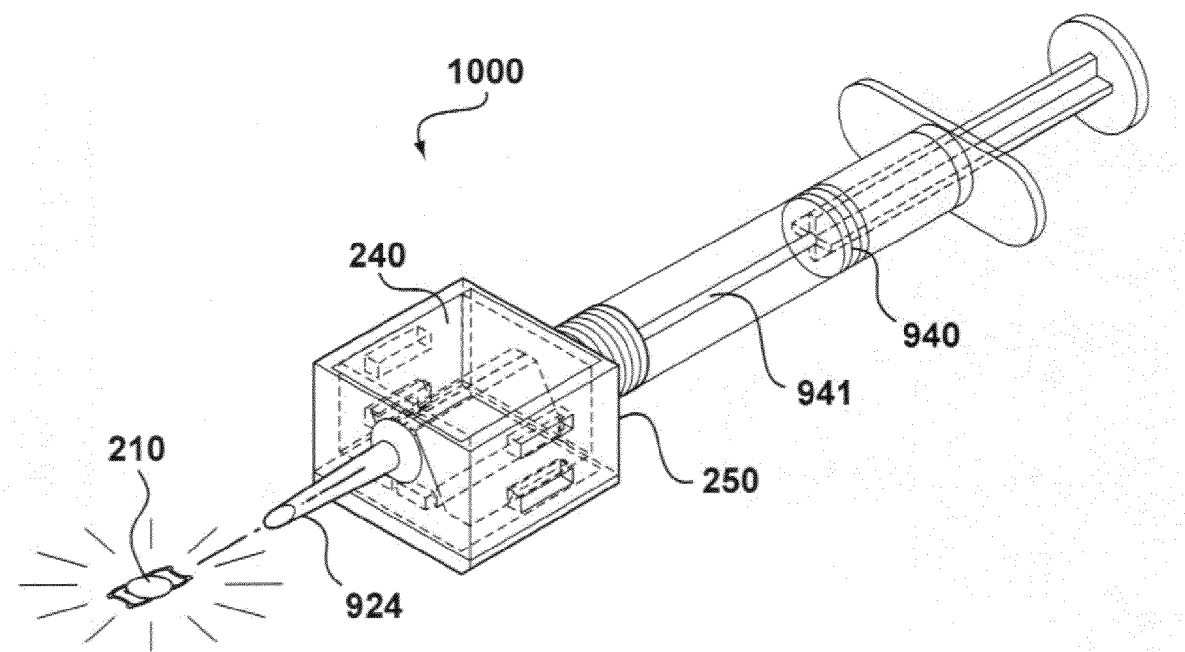
FIG. 9 is a perspective view of an assembly for insertion of a lens into an eye.

Referring to FIG. 9, nozzle 924 may be attached to one end of body 250 and a syringe, such as the stylus type syringe 940, may be attached to the opposite side of body 250. Syringe 940 may be collinear with folding guides 220 and 222 such that when the plunger of syringe 940 is pressed, a gelled fluid or, alternatively, a silicone-tipped push rod 941 in syringe 940 forces optic 210 into nozzle 924 for injection into a patient's eye.

In another embodiment, only one folding guide may be used. For instance, the concave inner face that was opposing one folding guide, such as guide 222 of FIG. 10C, can be part of body 250. Consequently, only one movable folding guide (220) would be needed. Driving cam 240 can be modified appropriately to move only one folding guide.

The material or materials for the components of system 1000 are preferably capable of withstanding high temperatures, such as those encountered in an autoclave. Moreover, the material for the shipping container should be such that it does not leach into the solution surrounding the lens, lest the lens be contaminated by the container material. Possible materials include polyolefins, nylon, Teflon and other plastics.

In another embodiment, a slipping agent (a material to reduce friction between surfaces) may be applied to one or more of the components of system 1000 to aid in the transition and/or injection processes. Such slipping agent may be any of or a combination of known slipping agents.

The body 250 of the system 1000 may contain a solution, such as saline, that provides a suitable environment for a medical implant (e.g., a lens). Body 250 may be sealable for shipping, or, instead, body 250 in the shipping mode may be placed within a sealable container for transport to the user. During shipment, system 1000 may or may not have the injection mechanism 924 or the injection actuation mechanism 940 attached to body 250.

Figure 10:
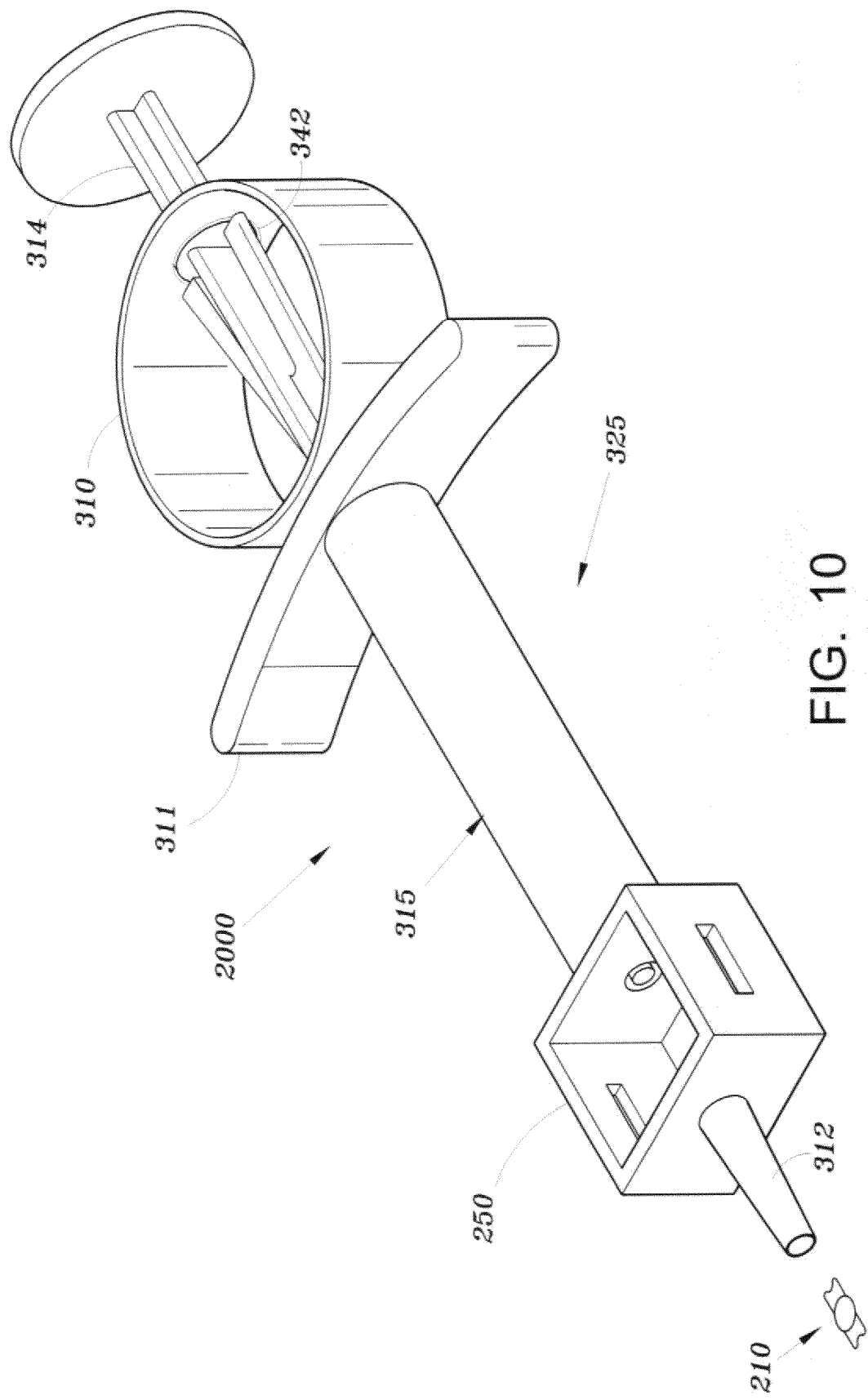
FIG. 10 is a perspective view of a second embodiment of an assembly for insertion of a lens into an eye.
Figure 16:
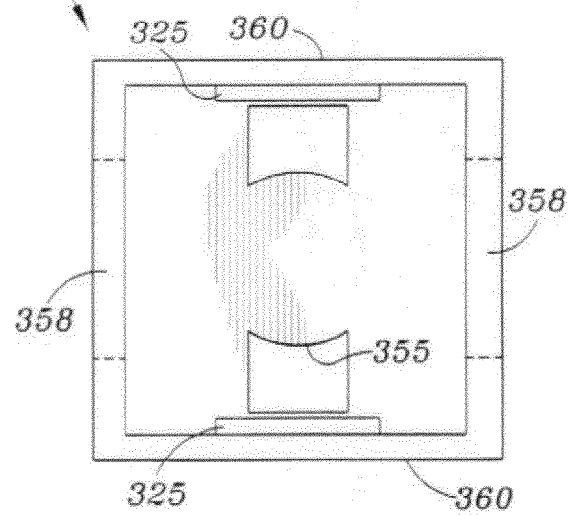
FIG. 16 is a top view of the body portion of the injector shown in FIG. 10.

An alternative embodiment of the insertion assembly is shown in FIG. 10. The assembly 2000 for insertion of the lens 210 includes body 350 which is adapted to receive the lens storing and folding assembly, as well as lens holder 230. As shown in FIGS. 10 and 16, body 350 is similar to body 250 of the first embodiment and includes upper and lower openings 358 and 360 respectively to receive detents 248 of driving cam 240. Body 350 also has openings 355 within its bottom to accommodate legs 234 and 236 of lens holder 230. Body 350 may also have attached thereto track guides 325, which may be disposed to allow key 224 to slide between track guide 325 and the bottom of body 350 as lens guides 220 and 222 move to fold an implantable device before it is displaced form body 350. A nozzle 312 extends outwardly from one side of the body and hollow cylindrical casing 315 extends from an opposite side of body 250. Formed integrally with the cylindrical casing 315 is flange member 311 that extends from opposite sides of the casing, which may be slightly arcuate. A resilient ring member 310 also formed integrally with the body portion extends outwardly from arcuate flange member 311 as shown in FIG. 10.

The nozzle 312, body 250, casing 315, flange 311 and ring 310 are preferably of a unitary, one piece construction, made of a suitable nylon material such as Vrydyne 21 SPF/21 SPG, sold by Solutia, Inc. However, other suitable materials include polyolefins, other nylons, Teflon and other plastics.

Figure 11:
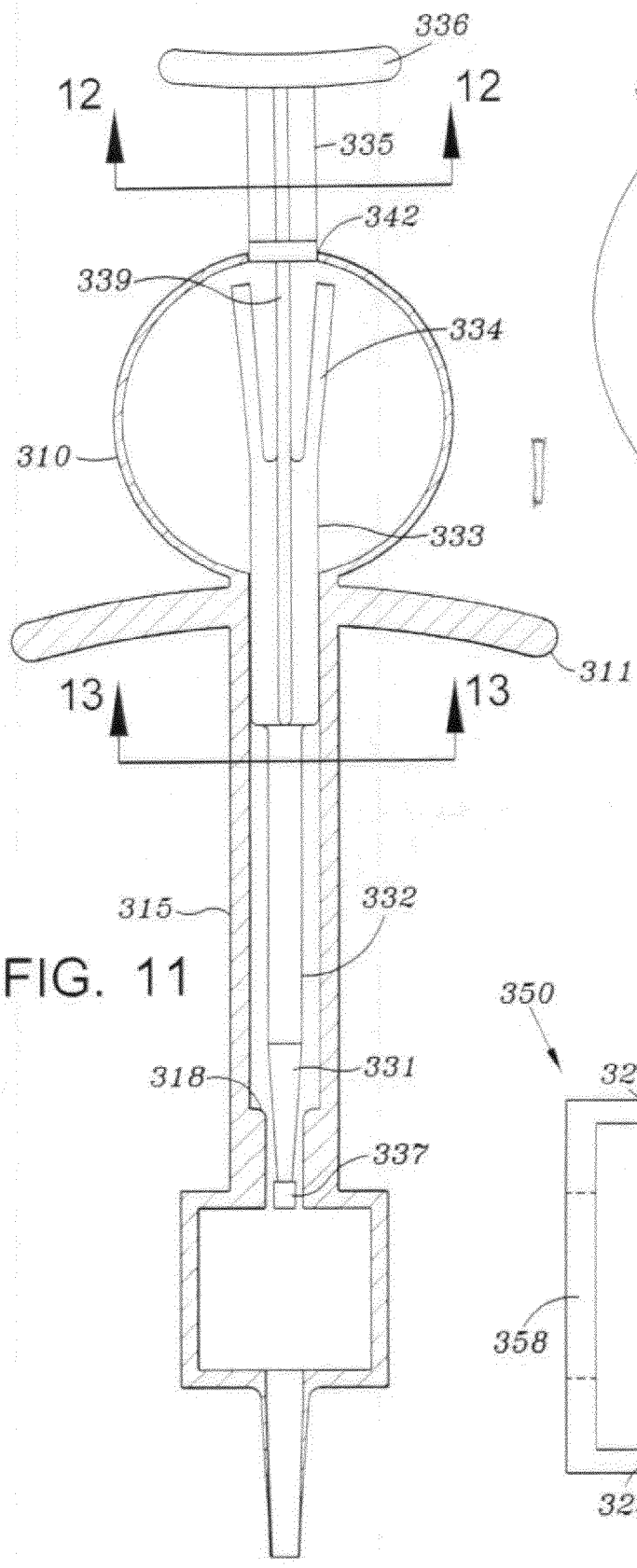
FIG. 11 is a cross sectional view of the housing of FIG. 10 with the plunger shown.
Figure 12:
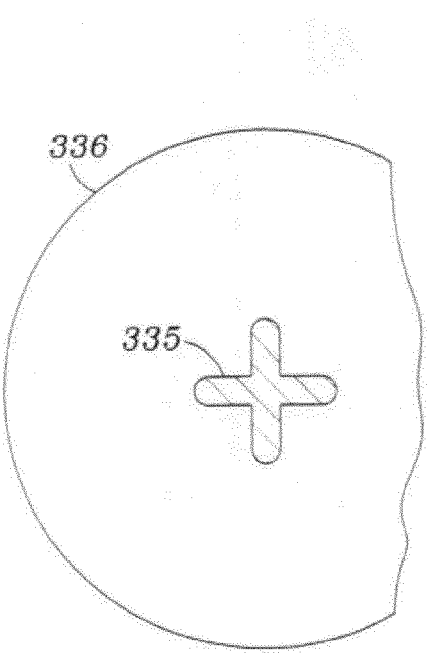
FIG. 12 is a cross sectional view along line 12 of FIG. 11.
Figure 13:
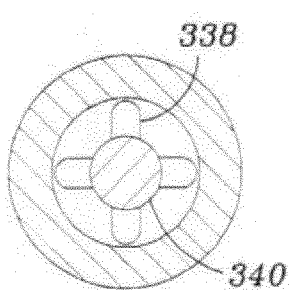
FIG. 13 is a cross sectional view of line 13 of FIG. 11.

As shown in FIG. 11, plunger 314 extends from thumb engaging portion 336 to a cylindrical tip 337 that pushes the ocular device through nozzle 312. A solid cylindrical portion 332 connects a lower tapered portion 331 with intermediate portion 333. Intermediate portion 333 has a x-shaped cross section.

The top portion of the intermediate plunger portion 333 has a flat planar section 339 and a plurality of resilient fingers 334 extending outwardly from the planar member 339. When the injector assembly is initially assembled, the plunger is inserted through a hole 342 extending through the upper portion of ring member 310 and then into the body portion 315. In their unflexed state, fingers 334 extend a distance outwardly from portion 333 greater than the diameter of hole 342. Thus as they engage hole 342, the fingers are compressed inwardly. Once they clear the hole, they return to their normal state and prohibit the plunger from being withdrawn from the body portion of the assembly. Fingers 334 are compressed inwardly as they enter the upper portion of casing 315 as shown in FIG. 14.

The upper portion of the plunger 335 has a x-shaped cross section and terminates in a circular disk portion 336 which is adapted to be engaged by the thumb of the surgeon. As shown in FIG. 15, as plunger 335 is depressed from its position shown in FIG. 14, enlarged position. 336 of the plunger engages ring member 310 and compresses the resilient ring until the plunger is in the position shown in FIG. 14. As pressure is released from the enlarged portion 336, the resilient spring will move the plunger toward the position shown in FIG. 14.

When the top portion 336 of the plunger initially engages ring 310, the tip 337 is positioned at the entrance of nozzle 312 as shown in FIG. 14. As the tip portion 337 passes through the outlet of nozzle 312, a shoulder portion 319 of the plunger abuts a shoulder 318 within casing 315 as shown in FIG. 15. This prevents further movement of the plunger within the eye.

The arrangement of FIGS. 10-15 allows the surgeon to inject the lens into the lens capsule, preferably using a pulsating technique. This technique involves the surgeon intermittently depressing the plunger and then releasing it. The IOL lens is moved along the interior of nozzle 312 in a series of discrete movements prior to being placed in the lens capsule. This overcomes the tendency of the haptics to bind between the nozzle and the cylindrical tip 337 of the plunger as the lens is being inserted.

The present invention has been described in terms of specific exemplary embodiments. In accordance with the present invention, the parameters for a system may be varied, typically with a design engineer specifying and selecting them for the desired application.

Further, it is contemplated that other embodiments, which may be devised readily by persons of ordinary skill in the art based on the teachings set forth herein, may be within the scope of the invention, which is defined by the appended claims. The present invention may be modified and practiced in different but equivalent manners that will be apparent to those skilled in the art and having the benefit of the teachings set forth herein.

We claim:

1. Apparatus for transporting and injecting a foldable medical device through an opening comprising:
   a body for containing the medical device;
   a nozzle extending from one side of the body;
   a plunger casing extending from a side of the body opposite the nozzle;
   a fingers-engaging flange extending outwardly from the portion of the plunger casing remote from the body;
   a plunger actuation control mechanism consisting of a single resilient ring member fixedly attached to and extending outwardly from the plunger casing;
   a plunger located with the plunger casing and extending through a hole in an upper portion of the resilient ring thereby compressing the ring member when the plunger is depressed,
   the plunger including a tip portion adapted to engage a foldable medical device supported within the body for injecting the device from the nozzle.

2. The apparatus of claim 1 wherein an upper portion of the plunger includes a plurality of resilient fingers that are radially deflected inwardly when the plunger is inserted through the hole in the upper portion of the ring member and then flex outwardly to prevent removal of the plunger from the casing.

3. The apparatus of claim 2 including a shoulder formed within the casing and a shoulder formed on the plunger such that the shoulders about each other when the device has been injected to prohibit further movement of the plunger.

4. The apparatus of claim 1 wherein the plunger has an enlarged portion at its proximal end that engages the upper portion of the resilient ring and compresses the resilient ring as the plunger is moved downwardly to inject the medical device.

5. Apparatus for transporting and injecting a foldable medical device through an opening comprising:
   a body for containing the medical device;
   a nozzle extending from one side of the body;
   a plunger casing extending from a side of the body opposite the nozzle;
   a fingers-engaging flange extending outwardly from the portion of the plunger casing remote from the body;
   a plunger actuation control mechanism consisting of a single resilient ring member fixedly attached to and extending outwardly from the plunger casing, said ring member extending in a plane that extends substantially parallel to a longitudinal axis of the plunger casing;
   a holder for the foldable device placed within the body;
   a folding guide located within the body;
   a driving cam located within the body for moving the folding guide when the cam is depressed;
   a plunger located in the plunger casing and extending through a hole in an upper portion of the resilient ring; and
   the plunger including at its upper end a thumb engaging portion having a dimension greater than the diameter of the hole in the upper portion of the resilient ring such that as the plunger is depressed, the thumb engaging portion engages the top portion of the resilient ring and compresses the ring as the plunger is moved inwardly.

6. The apparatus of claim 5 wherein the medical device is an intraocular lens supported by the holder in the body.

7. The apparatus of claim 6 wherein the folding guides comprises a semi-cylindrical concave surface adapted to surround the foldable medical device and fold the device as the surfaces move toward the device so as to form a cylinder.

8. The apparatus of claim 7 wherein the driving cam comprises sloping surfaces and is adapted to move the folding guides so as to fold the medical device when the driving cam is moved in a selected direction.

9. The apparatus of claim 8 wherein the body contains a track guide and the folding guide further comprises a key, the key being adapted to move within the track guides when the folding guide moves within the body.

10. The apparatus of claim 6 wherein the apparatus is first sterilized and then hermetically sealed.

* * * * *